United States Patent [19]

Grohe et al.

[11] Patent Number: 4,847,375

[45] Date of Patent: Jul. 11, 1989

[54] ANTIBACTERIAL 1,8-BRIDGED 4-QUINOLINE-3-CARBOXYLIC ACIDS

[75] Inventors: Klaus Grohe, Odenthal; Michael Schriewer, Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 874,249

[22] Filed: Jun. 13, 1986

[30] Foreign Application Priority Data

Jun. 22, 1985 [DE] Fed. Rep. of Germany ....... 3522405

[51] Int. Cl.$^4$ ............................................. C07D 265/36
[52] U.S. Cl. ........................................ 544/99; 544/71; 544/101
[58] Field of Search ............................ 544/71, 99, 101

[56] References Cited

U.S. PATENT DOCUMENTS

| | | | |
|---|---|---|---|
| 4,382,892 | 5/1983 | Hayakawa et al. | 544/101 X |
| 4,473,568 | 9/1984 | Hutt | 544/101 X |
| 4,571,396 | 2/1986 | Hutt et al. | 544/101 X |
| 4,725,595 | 2/1988 | Schriewer et al. | 544/99 X |
| 4,762,831 | 9/1988 | Grohe et al. | 544/99 X |
| 4,771,054 | 9/1988 | Domagala et al. | 544/101 X |

FOREIGN PATENT DOCUMENTS

| | | |
|---|---|---|
| 0047005 | 3/1982 | European Pat. Off. |
| 0101829 | 3/1984 | European Pat. Off. |
| 0107201 | 5/1984 | European Pat. Off. |
| 0115334 | 8/1984 | European Pat. Off. |
| 0160284 | 11/1985 | European Pat. Off. |
| 203085 | 12/1982 | Japan. |
| 204188 | 9/1986 | Japan. |

OTHER PUBLICATIONS

Chemical Abstracts, vol. 98, 1983, p. 635, abstract. No. 72117q, Columbus, Ohio, U.S.A.; Daiichi Seiyaku Co., Ltd. "8-Aminopyrido [1,2,3-de] [1,4] benzoxazine s", & JP-A-57 149 286 (Jpn. Kokai Tokkyo Koho) 14-9-1986.

Patent Abstracts of Japan, Band 8, No. 52 (C-213) [1489], 9 Mar. 1984 & JP-A-57 210 092 (Danchii) 07.12.1983.

Primary Examiner—Richard L. Raymond
Attorney, Agent, or Firm—Sprung Horn Kramer & Woods

[57] ABSTRACT

As antibacterials and animal growth promoters, the compounds of the formula

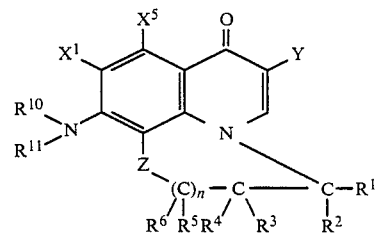

in which
Y is —COOH, —COOR$^7$ or —CONR$^8$, R$^9$,
X$^1$ is H, nitro, alkyl or halogen,
R$^{10}$ and R$^{11}$ preferably complete a piperazine ring,
Z is oxygen or NR$^{15}$,
n is 0 or 1, and
the others can have various meanings, and pharmaceutically acceptable hydrate, alkali metal, alkaline earth metal, silver or guanidinium salt or ester thereof.

5 Claims, No Drawings

ANTIBACTERIAL 1,8-BRIDGED 4-QUINOLINE-3-CARBOXYLIC ACIDS

The invention relates to new 1,8-bridged 4-quinolone-3-carboxylic acids, a process for their preparation and their use as medicaments, in particular as antibacterial agents in human and veterinary medicine.

The invention relates to new 1,8-bridged 4-quinolone-3-carboxylic acids and derivatives of the formula (I)

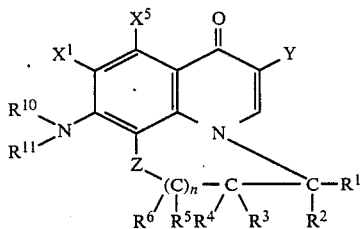

in which

Y represents a carboxyl group, a nitrile group, an ester group —COOR$^7$ or an acid amide group —CONR$^8$R$^9$,
wherein
R$^7$ represents C$_1$–C$_4$-alkyl and
R$^8$ and R$^9$ represent hydrogen or C$_1$–C$_4$-alkyl, and
R$^9$ can also be optionally substituted phenyl,
X$^1$ represents hydrogen, nitro, alkyl with 1 to 3 carbon atoms or halogen, preferably fluorine,
X$^5$ can be hydrogen, halogen or methyl,
R$^{10}$ and R$^{11}$, together with the nitrogen atom to which they are bonded, form a 5- or 6-membered heterocyclic ring, which can additionally contain the atoms or groups —O—, —S—, —SO—, —SO$_2$—,

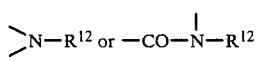

and which can optionally be mono-, di- or trisubstituted on the carbon atoms by C$_1$–C$_4$-alkyl, or by phenyl or cyclohexyl, optionally mono-, di- or trisubstituted by chlorine, fluorine, bromine, methyl, phenyl, hydroxyl, methoxy, benzyloxy, nitro or piperidino, or by 2-thienyl, hydroxyl, alkoxy with 1 to 3 carbon atoms, amino, methylamino, ethylamino, aminomethyl, methylaminomethyl or ethylaminomethyl,
wherein
R$^{12}$ represents hydrogen, a branched or straight-chain alkyl, alkenyl or alkinyl group which as 1 to 6 carbon atoms and can optionally be substituted by one or two hydroxyl, alkoxy, alkylamino or dialkylamino groups with 1 to 3 carbon atoms for an alkyl radical, the cyano group or the alkoxycarbonyl group with 1 to 4 carbon atoms in the alcohol part, a phenylalkyl group which has up to 4 carbon atoms in the aliphatic part and is optionally substituted in the phenyl radical, a phenacyl radical which is optionally mono- or disubstituted by hydroxyl, methoxy, chlorine or fluorine, or an oxoalkyl radical with up to 6 carbon atoms, or furthermore denotes a radical COR$^{13}$ or SO$_2$R$^{14}$,
wherein
R$^{13}$ denotes hydrogen, straight-chain or branched alkyl which has 1 to 4 carbon atoms and is optionally substituted by 1 to 2 substituents from the series comprising amino, alkoxycarbonyl with 1 to 3 carbon atoms in the alkyl part, carboxyl and alkoxy with 1 to 3 carbon atoms and halogen, such as chlorine, bromine and fluorine, or alkoxy with 1 to 4 carbon atoms, amino, alkylamino or dialkylamino with 1 to 5 carbon atoms in the alkyl part and
R$^{14}$ represents straight-chain or branched alkyl with 1 to 3 carbon atoms, and
Z represents oxygen or an amine radical NR$^{15}$,
wherein
R$^{15}$ denotes hydrogen, an alkyl radical which has 1 to 6 carbon atoms and is optionally substituted by halogen, trifluoromethyl, nitro, cyano, hydroxyl, alkoxy or alkylmercapto with 1–3 carbon atoms, aryloxy, arylthio or an ester radical with 1–3 carbon atoms in the alcohol part, or a phenyl radical which is optionally substituted by halogen, a nitro group, an alkyl group with 1–3 carbon atoms or an alkoxy or alkylmercapto group with in each case 1–3 carbon atoms, or furthermore represents an acyl radical R$^{16}$CO— or R$^{17}$SO$_2$—,
wherein
R$^{16}$ and R$^{17}$ represent alkyl radicals with 1–6 carbon atoms or optionally substituted phenyl radicals, or
R$^{15}$ can be a

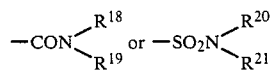

radical,
wherein
the radicals R$^{18}$ to R$^{21}$ represent hydrogen, alkyl with 1–6 carbon atoms or an optionally substituted phenyl radical;
and if (A) the symbol n is 0,
(a) R$^1$, R$^2$ and R$^3$ represent hydrogen, alkyl with 1–2 carbon atoms or phenyl and
R$^4$ represents CH$_2$X,
wherein
X represents halogen, cyano, hydroxyl or alkoxy or alkylmercapto which has 1–3 carbon atoms and is optionally substituted by phenyl,
(b) R$^1$ represents hydrogen, alkyl with 1–2 carbon atoms or phenyl,
R$^2$ represents CH$_2$X,
wherein
X represents halogen, cyano, hydroxyl or alkoxy or alkylmercapto which has 1–3 carbon atoms and is optionally substituted by phenyl,
R$^3$ represents hydrogen, alkyl with 1–3 carbon atoms or phenyl and
R$^4$ represents phenyl,
(c) R$^1$ and R$^2$ represent alkyl with 1–2 carbon atoms,
R$^3$ and R$^4$ represent hydrogen or alkyl which has 1–6 carbon atoms and is optionally substituted by phenyl, or represent phenyl,
(d) R$^1$ represents hydrogen,
R$^2$ represents hydrogen or alkyl with 1–2 carbon atoms,
R$^3$ represents hydrogen, alkyl which has 1–3 carbon atoms and is optionally substituted by phenyl or phenyl and
R$^4$ represents phenyl, and furthermore
(e) R$^1$ represents hydrogen,
R$^2$ represents aryl and
R$^3$ and R$^4$ represent hydrogen, alkyl or phenyl, (f) $R^1$ and $R^2$ represent hydrogen or alkyl with 1-2 carbon atoms and $R^3$ and $R^4$, with the carbon atom to which they are bnded, form a spirocyclic 3-7-membered ring and (g) $R^1$ and $R^2$, with the carbon atom to which they are bonded, form a spirocyclic 3-7-membered ring and $R^3$ and $R^4$ represent hydrogen, alkyl which has 1-6 carbon atoms and is optionally substituted by phenyl or phenyl, and furthermore (h) $R^2$ and $R^4$ represent hydrogen, alkyl with 1-6 carbon atoms or phenyl and $R^1$ and $R^3$, with the carbon atoms to which they are bonded, form a 3-7-membered ring, and if (B) the symbol n is 1, I. $R^1$ and $R^2$ represent hydrogen or alkyl with 1-2 carbon atoms and (a) $R^3$ and $R^4$ represent hydrogen and $R^5$ and $R^6$ represent alkyl which has 1-6 carbon atoms and is optionally sbustituted by phenyl, (b) $R^3$ and $R^4$ represent alkyl which has 1-6 carbon atoms and is optionally substituted by phenyl and $R^5$ and $R^6$ represent hydrogen, (c) $R^3$, $R^4$ and $R^5$ represent alkyl which has 1-6 carbon atoms and is optionally substituted by phenyl and $R^6$ represent hydrogen, (d) $R^4$, $R^5$ and $R^6$ represent alkyl which has 1-6 carbon atoms and is optionally substituted by phenyl and $R^3$ represents hydrogen, (e) $R^3$ to $R^6$ represent alkyl which has 1-6 carbon atoms and is optionally substituted by phenyl, (f) $R^3$ represents optionally substituted phenyl and $R^4$, $R^5$ and $R^6$ denotes hydrogen, (g) $R^5$ represents optionally substituted phenyl and $R^3$, $R^4$ and $R^6$ represent hydrogen, (h) $R^3$ and $R^6$ represent hydrogen and $R^4$ and $R^5$, with the carbon atoms to which they are bonded, form a 3-7-membered ring and (i) $R^3$ and $R^4$, with the carbon atom to which they are bonded, form a spirocyclic 3-7-membered ring and $R^5$ and $R^6$ represent hydrogen, alkyl with 1-3 carbon atoms or phenyl, (j) $R^5$ and $R^6$, with the carbon atom to which they are bonded, form a spirocyclic 3-7-membered ring and $R^3$ and $R^4$ represent hydrogen, alkyl with 1-3 carbon atoms or phenyl, (k) $R^3$ and $R^4$, and $R^5$ and $R^6$, with the particular carbon atoms to which they are bonded, form spirocyclic 3-7-membered rings, II. $R^1$ represents hydrogen.

$R^2$ and $R^3$, with the carbon atoms to which they are bonded, form a 3-7-membered ring and $R^4$, $R^5$ and $R^6$ represent hydrogen, alkyl with 1-6 carbon atoms or phenyl.

III. $R^1$ and $R^6$ represent hydrogen.

$R^2$ and $R^3$, and $R^4$ and $R^5$, in each case with the carbon atoms to which they are bonded, form a 3-7-membered ring, and IV. $R^1$ and $R^2$, with the carbon atom to which they are bonded, form a spirocyclic 3-7-membered ring and $R^3$ and $R^5$, with the carbon atoms to which they are bonded, form a 3-7-membered ring and $R^4$ and $R^6$ represent hydrogen or alkyl.

V. $R^1$ and $R^4$ represent hydrogen or alkyl with 1-2 carbon atoms, $R^2$ and $R^3$, with the carbon atoms to which they are bonded, form a 3-7-membered ring and $R^5$ and $R^6$, with the carbon atom to which they are bonded, form a spirocyclic 3-7-membered ring, and pharmaceutically usable hydrates and alkali metal, alkaline earth metal, silver and guanidinium salts thereof, and their esters which have a high antibacterial activity.

They are therefore suitable as active compounds for human and veterinary medicine, and above all as intermediate products for such bactericides.

Preferred compounds of the formula (I) are those in which

Y represents a carboxyl group, a nitrile group or an ester group $—COOR^7$, wherein $R^7$ can be methyl or ethyl, $X^1$ represents fluorine, $X^5$ represents hydrogen, $R^{10}$ and $R^{11}$, together with the nitrogen atom to which they are bonded, can form a 5- or 6-membered heterocyclic ring, which can additionally contain, as a ring member, an oxygen atom or the groups $N-R^{12}$ or $$-CO-\overset{|}{N}-R^{12},$$

and which can optionally be mono- or disubstituted on the carbon atoms by $C_1-C_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, wherein $R^{12}$ represents hydrogen, a branched or straight-chain alkyl group which has 1 to 3 carbon atoms and can optionally be substituted by one or two hydroxyl groups, a phenacyl radical, an oxoalkyl radical with up to 4 carbon atoms or a radical $COR^{13}$, wherein $R^{13}$ denotes hydrogen or alkyl with one or two carbon atoms, and Z represents oxygen or an amine radical $NR^{15}$, wherein $R^{15}$ represents an alkyl radical with 1-4 carbon atoms or a phenyl radical which is optionally substituted by halogen, methyl or nitro, and if $n=0$ or $n=1$, the abovementioned definitions apply for $R^1-R^6$.

The phenyl radicals can be substituted by halogen, alkyl with 1-3 carbon atoms, nitro, cyano, alkoxy or alkylmercapto with 1-3 carbon atoms, phenoxy, phenylthio or an ester group with 1-3 carbon atoms in the alcohol part.

The 3-7-membered rings formed by $R^1-R^6$ can be substituted by alkyl radicals with 1-3 carbon atoms or phenyl radicals.

It has furthermore been found that the compounds of the formula (I) are obtained by a process in which quinolonecarboxylic acid derivatives of the formula (II)

(II)

in which the radicals $X^1$, $X^5$, $R^1$-$R^6$, Z and n have the abovementioned meaning and $X^2$ preferably represents chlorine or fluorine, are reacted with amines of the formula (III)

$$\begin{matrix} R_{10} \\ \phantom{R} \\ R_{11} \end{matrix} \!\!\!\! NH \qquad (III)$$

in which $R_{10}$ and $R_{11}$ have the abovementioned meaning, if appropriate in the presence of acid-binding agents (method A).

Compounds of the formula (I) according to the invention can also be obtained by a process in which a 10-(1-piperazinyl)-compound (where n=0) or 11-(1-piperazinyl)-compound (where n=1) of the formula (IV)

(IV)

in which $X^1$, $X^5$, $R^1$-$R^6$, Z, Y and n have the abovementioned meaning and the piperazinyl radical can be mono-, di- or trisubstituted on the carbon atoms by $C_1$-$C_4$-alkyl, 2-thienyl or optionally substituted cyclohexyl or phenyl, is reacted with compounds of the formula (V)

$$R^{12}X \qquad (V)$$

in which $R^{12}$ has the abovementioned meaning, but cannot be hydrogen, and

X denotes fluorine, chlorine, bromine, iodine, hydroxyl, acyloxy, ethoxy, phenoxy or 4-nitrophenoxy, if appropriate in the presence of acid-binding agents (method B).

Compounds of the formula (I) according to the invention are also obtained by a process in which 10-(1-piperazinyl)-quinolonecarboxylic acid derivatives (n=0) or 11-(1-piperazinyl)-quinolonecarboxylic acid derivatives (n=1) of the formula (IV) in which the piperazinyl radical can be mono-, di- or trisubstituted on the carbon atoms by $C_1$-$C_4$-alkyl, 2-thienyl or optionally substituted cyclohexyl or phenyl, are reacted with Michael acceptors of the formula (VI)

$$B\text{—}CH\!\!=\!\!CH_2 \qquad (VI)$$

in which

B represents CN, CO—$R^{22}$ or COO$R^{23}$, wherein $R^{22}$ represents methyl or ethyl and $R^{23}$ represents methyl, ethyl or n- or i-propyl, (method C).

If 1-methyl-piperazine and 9,10-difluoro-2,3-dihydro-7-oxo-2-phenyl-7H-pyrido[1,2,3-de][1,4]-benzoaxazine-6carboxylic acid are used as the starting substance in the reaction according to method A, the course of the reaction can be represented by the following equation:

If ethyl iodide and 9-fluoro-2,3-dihydro-7-oxo-2-phenyl-10-(1-piperazinyl)-7H-pyrido[1,2,3-de][1,4]-benzoxazine-6-carboxylic acid are used as the starting substance in the reaction according to method B, the course of the reaction can be represented by the following equation:

If, for example, 9-fluoro-2,3-dihydro-7-oxo-2-phenyl-10-(1-piperazinyl)-7H-pyrido[1,2,3-de][1,4]-benzoxazine-6-carboxylic acid and methyl vinyl ketone are used as starting substances according to method C, the course of the reaction can be represented by the following equation:

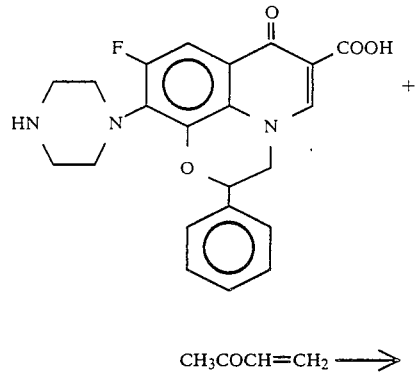

CH₃COCH=CH₂ ⟶

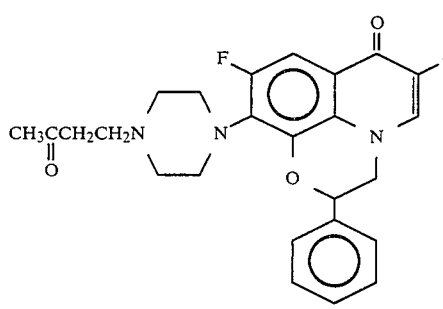

The quniolonecarboxylic acids of the formula (II) which can be used as starting substances according to method A can be prepared in accordance with the following equation:

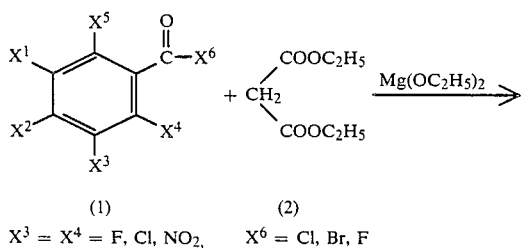

(1) (2)
$X^3 = X^4 = F, Cl, NO_2$, $X^6 = Cl, Br, F$

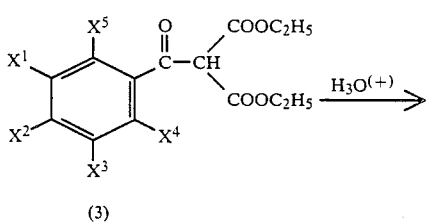

(3)

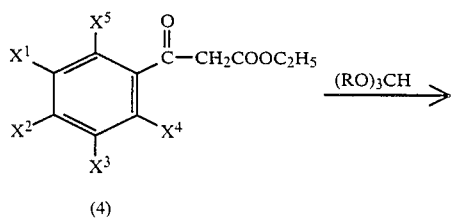

(4)

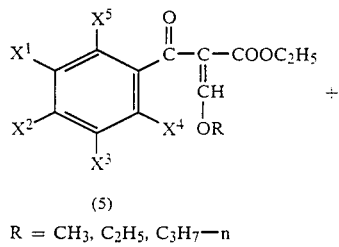

(5)
$R = CH_3, C_2H_5, C_3H_7-n$ $$H_2N-\underset{R^2}{\underset{|}{\overset{R^1}{\overset{|}{C}}}}-\underset{R^4}{\underset{|}{\overset{R^3}{\overset{|}{C}}}}-(\underset{R^6}{\underset{|}{\overset{R^5}{\overset{|}{C}}}})_n-ZH \xrightarrow{-ROH}$$

(6)
$R = CH_3, C_2H_5, C_3H_7-n$

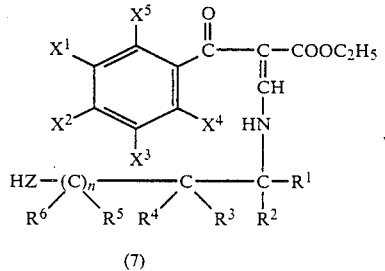

(7)

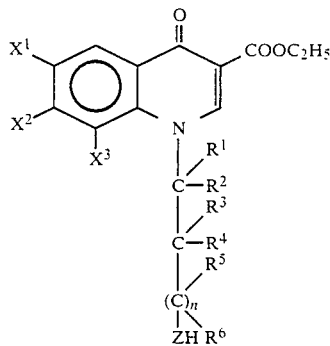

(8)

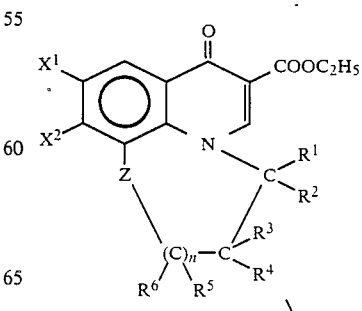

(9)

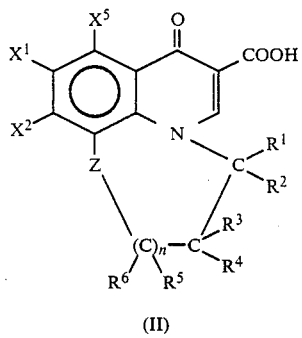

(II)

According to this equation, diethyl malonate (2) is acylated with the corresponding benzoyl fluoride or chloride (1) in the presence of magnesium ethylate to give the benzoylmalonate (3) (Organicum, 3rd edition 1964, page 438).

Partial hydrolysis and decarboxylation of (3) in an aqueous medium with catalytic amounts of sulphuric acid or p-toluenesulphonic acid gives a good yield of the ethyl benzoylacetate (4), which is converted with triethyl orthoformate/acetic anhydride into the ethyl 3-ethoxyacrylate (5). The reaction of (5) with the corresponding amine (6) in a solvent, such as, for example, methylene chloride, alcohol, chloroform, cyclohexane or toluene, leades to the desired intermediate product (7) in a slightly exothermic reaction.

The cyclization reactions (7)→(9) and (8)→(9) are carried out in a temperature range of about 60° to 300° C., preferably 80° to 180° C.

Diluents which can be used are dioxane, dimethylsulphoxide, N-methylpyrrolidone, sulpholane, hexamethylphosphoric acid triamide and, preferably, N,N-dimethylformamide.

Possible acid-binders for this reaction stage are potassium tert.-butanolate, butyl-lithium, lithium-phenyl, phenyl-magnesium bromide, sodium methylate, sodium hydride, sodium or potassium carbonate and, particularly preferably, potassium or sodium fluoride.

In general, in each case one equivalent of base is used for the primary cyclization (7)→(8) and the second cyclization (8)→(9).

If the two cyclization reactions are combined in a "one-pot reaction" (7)→(9), 2 equivalents of the above-mentioned bases must be employed. It may be advantageous to employ an excess of about 10 mol% of base in the cyclocondensations (7)→(9) and (8)→(9).

The hydrolysis of the esters (9) carried out in the last step to give the corresponding carboxylic acids can be carried out under the customary known acid or basic conditions.

The 2,3,4,5-tetrafluorobenzoyl chloride or the pentafluorobenzoyl chloride used as starting substances for this synthesis route are known.

3,5-Dichloro-2,4-difluoro-benzoyl fluoride (boiling point 97°/20 mbar; $n_D^{20}=1.5148$) and 5-chloro-2,3,4-trifluorobenzoyl fluoride (boiling point 66°–70°/20 mbar; $n_D^{20}=1.4764$) are obtained side by side when tetrachlorobenzoyl chloride is heated to elevated temperatures with potassium fluoride in sulpholane:

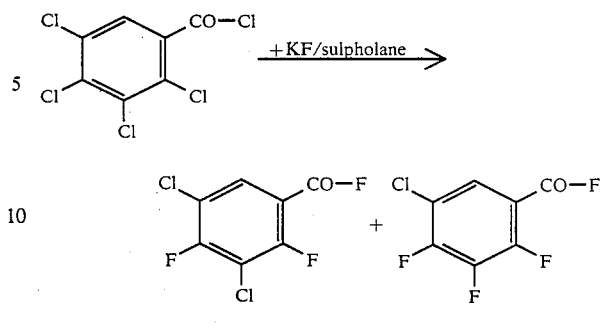

The chlorination of 2,4,5-trifluorobenzoic acid in chlorosulphonic acid leads to 3-chloro-2,4,5-trifluorobenzoic acid, which is reacted as a crude product with thionyl chloride to give 3-chloro-2,4,5-trifluorobenzoyl chloride (boiling point 94°/18 mbar; $n_D^{20}=1.5164$):

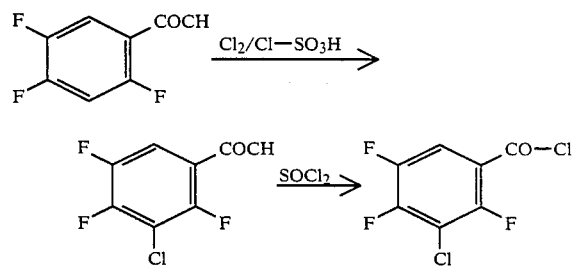

The 2,4-dichloro-5-fluoro-3-nitro-benzoyl chloride is obtained by nitration of 2,4-dichloro-5-fluoro-benzoic acid, which is known, to 2,4-dichloro-5-fluoro-3-nitrobenzoic acid and reaction thereof with thionyl chloride.

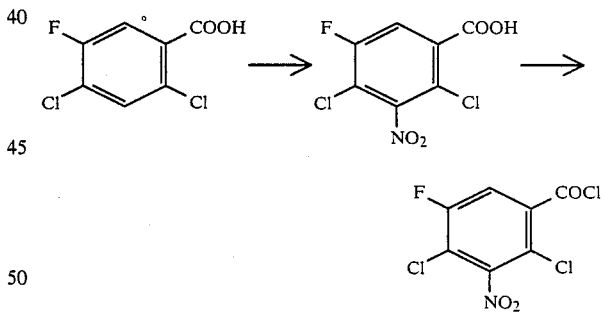

The amines of the formula (6) used as starting substances are known. Examples which may be mentioned are: 2-aminocyclopentanol, 2-aminocyclohexanol, 2-(2-aminoethylamino)-ethanol, 2-amino-2-phenylethanol, 1-amino-2,3-propanediol, 2-amino-3-phenylpropanol, 2-amino-1-phenyl-1,3-propanediol, N-phenyl-ethylenediamine, N-benzyl-ethylenediamine and 2-aminomethylcyclohexanol.

The amines (III) used as starting substances are known or can be obtained by processes which are known from the literature [U.S. Pat. No. 4,166,180 and J. Med. Chem. 26, 1116 (1983)]. Catalytic hydrogenation of the 2-aryl-piperazines gives the corresponding 2-cyclohexyl-piperazines: for example: 2-cyclohexyl-piperazine (waxy, melting point 71°–73° C.). Examples which may be mentioned are: morpholine, piperidine, thiomorpholine, pyrrolidine, piperazine, N-methylpiperazine, N-ethylpiperazine, N-(2-hydroxyethyl)piperazine, N-formylpiperazine, 2-methylpiperazine, 1,2-dimethylpiperazine, cis- and trans-2,5-dimethylpiperazine, cis- and trans-2,6-dimethylpiperazine, 2-ethylpiperazine, 2-propylpiperazine, 2-isopropylpiperazine, 2-isobutylpiperazine, 2-piperazinone, 1-methyl-2-piperazinone, 1-ethyl-2-piperazinone, 2-cyclohexylpiperazine, 2-phenylpiperazine, 2-(4-chlorophenyl)-piperazine, 2-(4-fluorophenyl)-piperazine, 2-(4-bromophenyl)-piperazine, 2-(4-methylphenyl)-piperazine, 2-(4-biphenyl)-piperazine, 2-(4-methoxyphenyl)-piperazine, 2-(4-benzyloxyphenyl)-piperazine, 2-(4-hydroxyphenyl)-piperazine, 2-(4-nitrophenyl)-piperazine, 2-(3-nitrophenyl)-piperazine, 2-(4-piperidinophenyl)-piperazine, 2-(3,4-dimethoxyphenyl)-piperazine, 2-(3,4,5-trimethoxyphenyl)-piperazine, 2-(3,4-dimethoxy-6-methyl)-piperazine, 2-(2-thienyl)-piperazine and 3-amino-pyrrolidine.

The compounds of the formula (V) used as starting substances are known. Examples which may be mentioned are: methyl iodide, methyl bromide, ethyl iodide, ethyl bromide, ethyl chloride, 2-hydroxyethyl chloride, 3-hydroxypropyl chloride, 4-hydroxybutyl chloride, n-propyl brmoide, i-propyl iodide, n-butyl bromide, i-butyl bromide, sec.-butyl chloride, n-pentyl chloride, 3-methylbutyl chloride and n-hexyl bromide. Formic acid/acetic acid anhydride, acetic anhydride, propionic anhydride, acetyl chloride, chloroacetyl chloride, dichloroacetyl chloride, bromoacetyl bromide, butyryl chloride, 4-chlorobutyryl chloride, isobutyryl chloride, N-(tert.-butoxycarbonylglycine 4-nitrophenyl ester, N-(tert.-butoxycarbonyl)-L-alanine 4-nitro-phenyl ester, N-(tert.-butoxycarbonyl)-L-Leucine 4-nitro-phenyl ester, N-(tert.-butoxycarbonyl)-L-valine 4-nitro-phenyl ester, 3-methoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethylcarbamyl chloride, methanesulphonyl chloride, ethanesulphonyl chloride, propane-1-sulphonyl chloride and formic acid.

The compounds of the formula (VI) whcih can be used according to the invention are known. Examples which may be mentioned are: acrylonitrile, methyl vinyl ketone, methyl acrylate and ethyl acrylate.

The reaction of (II) with (III) according to method A is preferably carried out in a diluent, such as dimethylsulphoxide, N,N-dimethylformamide, hexamethylphosphoric acid trisamide, sulpholane, water, an alcohol, such as methanol, ethanol, n-propanol, isopropanol or glycol monomethyl ether, or pyridine. Mixtures of these diluents can also be used.

All the customary inorganic and organic acid-binding agents can be used as acid-binding agents. These include, preferably, the alkali metal hydroxides, alkali metal carbonates, organic amines and amidines. The following may be mentioned specifically as being particularly suitable: triethylamine, 1,4-diaza-bicyclo[2,2,2]-octane (DABCO), 1,8diaza-bicyclo[5,4,0]-undec-7-ene (DBU) or excess amine (III).

The reaction temperatures can be varied within a substantial range. The reaction is in general carried out between about 20° and 200° C., preferably between 80° and 180° C.

The reaction can be carried out under normal pressure, but also under increased pressure. It is in general carried out under pressures between about 1 and about 100 bar, preferably between 1 and 10 bar.

In carrying out the process according to the invention, 1 to 15 moles, preferably 1 to 6 moles, of the amine (III) are employed per mole of the carboxylic acid (II).

The reaction of (IV) with (V) is preferably carried out in a diluent, such as dimethylsulphoxide, dioxane, N,N-dimethylformamide, hexamethyl-phosphoric acid trisamide, sulpholane, water, and alcohol, such as methanol, ethanol, n-propanol, isopropanol or glycol monomethyl ether, or pyridine. Mixtures of these diluents can also be used.

All the customary inorganic and organic acid-binding agents can be used as the acid-binding agents. These include, preferably, the alkali metal hydroxides, alkali metal carbonates, organic amines and amidines. The following may be mentioned specifically as being particularly suitable: triethylamine, 1,4-diazabicyclo[2,2,2]-octane (DABCO) or 1,8-diazabicyclo-[5,4,0]undec-7-ene (DBU).

The reaction temperatures can be varied within a substantial range. The reaction is in general carried out between about 20° and about 180° C., preferably between 40° and 110° C.

The reaction can be carried out under normal pressure, but also under increased pressure. It is in general carried out under pressures between about 1 and about 100 bar, preferably between 1 and 10 bar.

In carrying out the process according to the invention in method B, 1 to 4 moles, preferably 1 to 1.5 moles, of the compound (V) are employed per mole of the compound (IV).

The reaction of (IV) with (VI) (method C) is preferably carried out in a diluent, such as dioxane, dimethylsulphoxide, N,N-dimethylformamide, methanol, ethanol, isopropanol, n-propanol or glycol monomethyl ether, or in mixtures of these diluents.

The reaction temperatures can be varied within a substantial range. The reaction is in general carried out between about 20° C. and about 150° C., preferably between 50° C. and 100° C.

The reaction can be carried out under normal pressure, or also under increased pressure. It is in general carried out under presures between about 1 and about 100 bar, preferably between 1 and 10 bar.

In carrying out the process according to the invention by method C, 1 to 5 moles, preferably 1 to 2 moles, of the compound (VI) are employed per mole of the compound (IV).

The following may be mentioned specifically as new active compounds, in addition to the compounds listed in the examples: 9-fluoro-2,3-dihydro-10-(4-methyl-1-piperazinyl)-7-oxo-3-phenyl-7H-pyrido[1,2,3-de][1,4-]benzoxazine-6-carboxylic acid, 9-fluoro-2,3-dihydro-7-oxo-3-phenyl-10-(1-piperazinyl)-7H-pyrido[1,2,3-de][1,4]benzoxazine-6-carboxylic acid, 9-fluoro-2,3-dihydro-2-hydroxymethyl-10-(4-methyl-1-piperazinyl)-7-oxo-7H-pyrido[1,2,3-de][1,4]-benzoxazine-6carboxylic acid, 9-chloro-2,3-dihydro-2-hydroxymethyl-10-(4-methyl-1-piperazinyl)-7-oxo-7H-pyrido-[1,2,3-de][1,4-]benzoxazine-6carboxylic acid, 9-chloro-2,3-dihydro-7-oxo-2-phenyl-10-(1-pyrrolidinyl)-7H-pyrido-[1,2,3-de][1,4]-benzoxazine-6-carboxylic acid, 9-fluoro-2,3-dihydro-7-oxo-2-phenyl-10-(1-pyrrolidinyl)-7H-pyrido-[1,2,3-de][1,4]benzoxazine-6-carboxylic acid, 6-fluoro-3a,11a-dihydro-8-oxo-5-(1-pyrrolidinyl)-8H-cyclopenta-[1,2-b]pyrido[1,2,3-de][1,4]benzoxazine-9carboxylic acid, 6-chloro-3a,11a-dihydro-8oxo-5(1-pyrrolidinyl)-8H-cyclopenta[1,2-b]pyrido[1,2,3-de][1,4]benzoxazine-9carboxylic acid, 9-fluoro-2,3-dihydro-3,3-dimethyl-7- oxo-10-(1-pyrrolidinyl)-7H-pyrido[1,2,3-de][1,4]benzoxazine-6-carboxylic acid, 9-chloro-2,3-dihydro-3,3-dimethyl-7-oxo-10-(1-pyrrolidinyl)-7H-pyrido[1,2,3-de][1,4]benzoxazine-6-carboxylic acid, 9-chloro-2,3-dihydro-3,3-dimethyl-7-oxo-10-(3-phenyl-1-piperazinyl)-7H-pyrido[1,2,3-de][1,4]benzoxazine-6-carboxylic acid, 6-fluoro-3a,11a-dihydro-8-oxo-5(3-phenyl-1-piperazinyl)-8H-cyclopenta[1,2-b]pyrido[1,2,3-de][1,4]-benzoxazine-9-carboxylic acid and 9-fluoro-2-fluoromethyl-2,3-dihydro-7-oxo-10-(1-pyrrolidinyl)-7H-pyrido[1,2,3-de]-[1,4]benzoxazine-6-carboylic acid.

Example of a tablet according to the invention

Each tablet contains:

| | |
|---|---|
| Compound of Example 1 | 583.0 mg |
| Microcrystalline cellulose | 55.0 mg |
| Corn starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |

The lacquer shell contains:

| | |
|---|---|
| Poly-(O—hydroxypropyl-O—methyl)-cellulose 15 cp | 6.0 mg |
| Macrogol 4000 recommended INN polyethylene glycols (DAB) | 2.0 mg |
| Titanium-(IV) oxide | 2.0 mg |
| | 10.0 mg |

The compounds according to the invention exhibit a broad antibacterial spectrum against Gram-positive and Gram-negative germs, in particular against Enterobacteriaceae: above all also against those which are resistant towards various antibiotics, such as, for example, penicillins, cephalosporins, aminoglycosides, sulphonamides and tetracyclines, coupled with a low toxicity.

These useful properties enable them to be used as chemotherapeutic active compounds in medicine and as substances for preserving inorganic and organic materials, in particular all types of organic materials, for example polymers, lubricants, paints, fibers leather, paper and wood, and foodstuffs and water.

The compounds according to the invention are active against a very broad spectrum of microorganisms. Gram-negative and Gram-positive bacteria and bacteria-like microorganisms can be combated and the diseases caused by these pathogens can be prevented, alleviated and/or cured with the aid of these compounds.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases caused by the following pathogens or by mixtures of the following pathogens can be treated and/or prevented:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*): Gram-negative cocci (*Neisseria gonorrhoeae*) and Gram-negative rod-shaped bacillae, such as Enterobacteriaceae, for example *Escherichia coli, Haemophilus influenzae, Citrobacter* (*Citro. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia, and the genus Acinetobacter. The antibacterial spectrum moreover includes the genus Pseudomonas (*Ps. aeruginosa* and *Ps. maltophilia*) as well as strictly anaerobic bacteria, such as, for example, *Bacteroides fragilis*, representatives of the genus Peptococcus, Peptostreptococcus and the genus Clostridium: and furthermore mycoplasms (*M. pneumoniae, M. hominis* and *M. urealyticum*) and mycobacteria, for example *Mycobacterium tuberculosis*.

The above list of pathogens is purely by way of example and is in no way to be interpreted as limitative. Examples which may be mentioned of diseases which can be prevented, alleviated and/or cured by the compounds according to the invention are: otitis; pharyngitis: pneumonia: peritonitis: pyelonephritis: cystitis: endocarditis: systemic infections: bronchitis: arthritis: local infections: and septic diseases.

The present invention includes pharmaceutical formulations which, in addition to non-toxic, inert pharmaceutically suitable excipients, contain one or more compounds according to the invention or consist of one or more compounds according to the invention, and to processes for the preparation of these formulations.

The present invention also includes pharmaceutical formulations in dosage units, this means that the formulation are in the form of individual parts, for example tablets, dragees, capsules, pills, suppositories and ampules, the active compound content of which correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half, one third or one quarter of a daily dose.

By non-toxic, inert pharmaceutically suitable excipients there are to be understood solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds, alongside the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only or preferentially in a certain part of the intestinal tract, optionally in a delayed manner, examples of embedding compositions which can be used being polymeric substances and waxes.

The active compound or compounds, optionally with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colorants, preservatives and additives which improve the odour and flavour, for example peppermint oil and eucalyptus oil, or sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds, in addition to compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100, mg/kg of body weight every 24 hours, if appropriate in the form of several individual doses, to achieve the desired results. An individual dose preferably contains the active compound or compounds in amounts of about 1 to about 250, in particular 3 to 60, mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus in some cases it may be sufficient to manage with less than the abovementioned amount of active compound, while in other cases the abovementioned amount of active compound must be exceeded. The particular optimum dosage required and mode of administration of the active compounds can easily be specified by any expert on the basis of his expert knowledge.

The new compounds can be administered to animals in the customary concentrations and formulations together with the feed or with feed formulations or with the drinking water. Infection by Gram-negative or Gram-positive bacteria can thereby be prevented, alleviated and/or cured and promotion in growth and an improvement in feed utilization can thereby be achieved.

The MIC values of some of the compounds according to the invention are given in the following table.

| Strain | MIC (mcg/ml) Example No. 7 | Example No. 3 |
| --- | --- | --- |
| E. coli Neumann | 1 | 2 |
| E. coli T 7 | 0.5 | 2 |
| E. coli A 261 | 0.125 | 2 |
| Klebsiella 8085 | 0.25 | 2 |
| Agar dilution test (Isosensitest medium); Denley multi-point inoculator | | |

The following examples illustrate the invention:

EXAMPLE 1

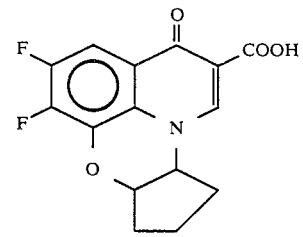

(a) 6.4 g of ethyl 3-ethoxy-2-(2,3,4,5-tetrafluorobenzoyl)-acrylate are initially introduced into 8 ml of ehtanol. A solution of 2.5 g of 2-aminocyclopentanol in 15 ml of ethanol is added dropwise, while cooling with ice. The mixture is stirred at room temperature for a further two hours and then concentrated in vacuo. 8.3 g of ethyl (2-(2,3,4,5-tetrafluorobenzoyl)-3-(2-hydroxycyclopentyl)aminoacrylate remain as a crude oil.

(b) 8 g of the product from (a) are heated at 140°–45° in 40 ml of dimethylformamide with 3.3 g of potassium carbonate for 4 hours. After cooling to room temperature, the mixture is diluted with water and cooled. The precipitate formed is separated off and, if appropriate, recrystallized from glycol monomethyl ether. Yield: 5.4 g of ethyl 5,6-difluoro-3a,11a-dihydro-8-oxo-8H-cyclopenta[1,2-b]pyrido[1,2,3-d,e]-[1,4]-benzoxazine-9-carboxylate.

Melting point: 255°–58°

(c) 5.4 g of the product from (b) are heated at 140° C. (bath) in a mixture of 17 ml of acetic acid, 16 ml of water and 1.6 ml of concentrated sulphuric acid for 4 hours. The mixture is then cooled and diluted with water and the solid is isolated.

Yield: 4.4 g of 5,6-difluoro-3a,11a-dihydro-8-oxo-8H-cyclopental[1,2-b]-pyrido[1,2,3-d,e]-[1,4]-benzoxazine-9-carboxylic acid Melting point: 270° (decomposition)

EXAMPLE 2

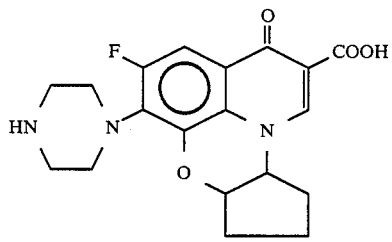

1.4 g of the product from Example 1 and 1.94 g of piperazine are heated at 140° C. in 14 ml of DMSO for 2.5 hours. Thereafter, the solvent is distilled off under a high vacuum. The residue is boiled up with ethanol and the solid is isolated.

Yield: 1.6 g of 6-fluoro-3a,11a-dihydro-8-oxo-5-(1-piperazinyl)-8H-cyclopenta[1,2-b]-pyrido[1,2,3-d,e]-[1,4]-benzoxazine-9carboxylic acid.

Melting point: 252°–4°

The following quinolonecarboxylic acids of the formula (I) were obtained analogously to Exmaple 2 (Table 1):

scope of the invention will suggest themselves to those skilled in the art.

We claim:

1. A 1,8-bridged 4-quinolone-3-carboxylic acid or derivative thereof of the formula

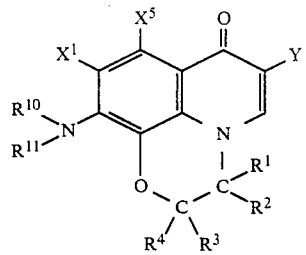

in which

Y represents a carboxyl group, a nitrile group, an ester group —COOR⁷ or an acid amide group —CONR⁸R⁹, wherein $R^7$ represents $C_1$–$C_4$-alkyl and $R^8$ and $R^9$ represent hydrogen or $C_1$–$C_4$-alkyl, and $R^9$ can also be phenyl, $X^1$ represents hydrogen, nitro, alkyl with 1 to 3 carbon atoms or halogen, $X^5$ can be hydrogen, halogen or methyl, $R^{10}$ and $R^{11}$, together with the nitrogen atom to which they are bonded, form a 5- or 6-membered heterocyclic ring, which can additionally contain the atoms or groups -0-,

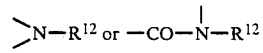

and which can optionally be mono-, di- or trisubstituted on the carbon atoms by $C_1$–$C_4$-alkyl, or by phenyl or cyclohexyl, optionally mono-, di- or trisubstituted by chlorine, fluorine, bromine, methyl, phenyl, hydroxyl, methoxy, benzyloxy, nitro or piperidino, or by 2-thienyl, hydroxyl, alkoxy with 1 to 3 carbon atoms, amino, methylamino, ethylamino, aminomethyl, methylaminomethyl or ethylaminomethyl,

TABLE 1

| | | | | | | | Quinolonecarboxylic acids of the formula (I) Z = O. X¹ = F. X⁵ = H. Y = COOH | |
|---|---|---|---|---|---|---|---|---|
| Example | R¹ | R² | R³ | R⁴ | R⁵ | R⁶ | R¹⁰ R¹¹ | Melting point |
| 3 | H | —(CH₂)₃— | | H | | | —CH₂CH₂—N(CH₃)—CH₂CH₂— | 210-20° |
| 4 | H | —(CH₂)₄— | | H | | | —CH₂CH(CH₃)—NH—CH₂—CH₂— | 248-50° |
| 5 | —(CH₂)₅— | | H | H | | | —CH₂CH₂—NH—CH₂—CH₂— | 148-51° |
| 6 | —(CH₂)₅— | | H | H | | | —CH₂CH₂—N(CH₃)—CH₂CH₂— | 242-4° |
| 7 | CH₃ | CH₃ | H | H | | | —CH₂CH₂—NH—CH₂CH₂— | 264-6° (decomp.) |
| 8 | CH₃ | CH₃ | H | H | | | —CH₂CH₂—N(CH₃)—CH₂CH₂— | 272-4° |
| 9 | H | —(CH₂)₅— | | H | | | —CH₂CH₂—NH—CH₂CH₂— | 191-3° |
| 10 | H | —(CH₂)₅— | | H | | | —CH₂CH₂—N(CH₃)—CH₂CH₂— | 214-6° |
| 11 | H | H | CH₂F | H | | | —CH₂CH₂—NH—CH₂CH₂— | 252-4° |
| 12 | H | H | CH₂F | H | | | —CH₂CH₂—N(CH₃)—CH₂CH₂— | 264-6° (decomp.) |
| 13 | H | H | Ph | H | | | —CH₂CH₂—NH—CH₂CH₂— | 234-6° (decomp.) |
| 14 | H | H | Ph | H | | | —CH₂CH₂—N(CH₃)—CH₂CH₂— | 244-6° |
| 15 | H | H | Ph | H | | | —CH₂CH(CH₃)—NH—CH₂CH₂— | 240° (decomp.) |
| 16 | H | H | —(CH₂)₄— | | H | H | .—CH₂CH₂—NH—CH₂CH₂— | 78-80° |
| 17 | H | H | —(CH₂)₄— | | H | H | —CH₂CH₂—N(CH₃)—CH₂CH₂— | 158-61° |

It is understood that the specification and examples are illustrative but not limitative of the present invention and that other embodiments within the spirit and wherein $R^{12}$ represents hydrogen, a branched or straight-chain alkyl, alkenyl or alkinyl group which has up to 6 carbon atoms and can optionally be substituted by one or two hydroxyl, alkoxy, alkylamino or dialkylamino groups with 1 to 3 carbon atoms for an alkyl radical, the cyano group or the alkoxycarbonyl group with 1 to 4 carbon atoms in the alcohol part, a phenylalkyl group which has up to 4 carbon atoms in the aliphatic part, a phenacyl radical which is optionally mono- or disubstituted by hydroxyl, methoxy, chlorine or fluorine, or an oxoalkyl radical with up to 6 carbon atoms, or furthermore denotes a radical $COR^{13}$ or $SO_2R^{14}$, wherein $R^{13}$ denotes hydrogen, straight-chain or branched alkyl which has 1 to 4 carbon atoms and is optionally substituted by 1 or 2 substituents from the series comprising amino, alkoxycarbonyl with 1 to 3 carbon atoms in the alkyl part, carboxyl and alkoxy with 1 to 3 carbon atoms and halogen, or alkoxy with 1 to 4 carbon atoms, amino, alkylamino or dialkyl-1 to 4 carbon atoms, amino, alkylamino or dialkylamino with 1 to 5 carbon atoms in the alkyl part and $R^{14}$ represents straight-chain or branched alkyl with 1 to 3 carbon atoms, and (a) $R^1$, $R^2$ and $R^3$ represent hydrogen, alkyl with 1-2 carbon atoms or phenyl and $R^4$ represents $CH_2X$, wherein X represents halogen, cyano, hydroxyl or alkoxy or alkylmercapto which has 1-3 carbon atoms and is optionally substituted by phenyl, (b) $R^1$ represents hydrogen, alkyl with 1-2 carbon atoms or phenyl, $R^2$ represents $CH_2X$, wherein X represents halogen, cyano, hydroxyl or alkoxy or alkylmercapto which has 1-3 carbon atoms and is optionally substituted by phenyl, $R^3$ represents hydrogen, alkyl with 1-3 carbon atoms or phenyl and $R^4$ represents vinyl, (c) $R^1$ and $R^2$ represent alkyl with 1-2 carbon atoms, $R^3$ and $R^4$ represent hydrogen or alkyl which has 1-6 carbon atoms and is optionally substituted by phenyl, or represent phenyl, provided at least one of $R^3$ and $R^4$ is phenyl or alkylphenyl, (d) $R^1$ represents hydrogen, $R^2$ represents hydrogen or alkyl with 1-2 carbon atoms, $R^3$ represents hydrogen, alkyl which has 1-3 carbon atoms and is optionally substituted by phenyl or phenyl and $R^4$ represents phenyl, and furthermore (e) $R^1$ represents hydrogen $R^2$ represents aryl and $R^3$ and $R^4$ represent hydrogen, alkyl or phenyl, (f) $R^1$ and $R^2$ represent hydrogen or alkyl with 1-2 carbon atoms and $R^3$ and $R^4$, with the carbon atom to which they are bonded, form a spirocyclic 3-7-membered ring and (g) $R^1$ and $R^2$, with the carbon atom to which they are bonded, form a spirocyclic 3-7-membered ring and $R^3$ and $R^4$ represent hydrogen, alkyl which has 1-6 carbon atoms and is optionally substituted by phenyl or phenyl, and furthermore (h) $R^2$ and $R^4$ represent hydrogen, alkyl with 1-6 carbon atoms or phenyl and $R^1$ and $R^3$, with the carbon atoms to which they are bonded, form a 3-7-membered ring, or a pharmaceutically acceptable hydrate, alkali metal, alkaline earth metal, silver or guanidinium salt or ester thereof.

2. A 1,8-bridged 4-quinolone-3-carboxylic acid, derivative, hydrate, salt or ester according to claim 1, in which Y represents a carboxyl group, a nitrile group or an ester group $—COOR^7$, wherein $R^7$ can be methyl or ethyl, $X^1$ represents fluorine, $X^5$ represents hydrogen, $R^{10}$ and $R^{11}$, together with the nitrogen atom to which they are bonded, can form a 5- or 6-membered heterocyclic ring, which can additionally contain, as a ring member, an oxygen atom or the groups $N-R^{12}$ or

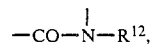

and which can optionally be mono- or disubstituted on the carbon atoms by $C_1-C_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, $R^{12}$ represents hydrogen, a branched or straight-chain alkyl group which has 1 to 3 carbon atoms and can optionally be substituted by one or two hydroxyl groups, a phenacyl radical an oxoalkyl radical with up to 4 carbon atoms or a radical $COR^{13}$, wherein $R^{13}$ denotes hydrogen or alkyl with one or two carbon atoms.

3. A compound according to claim 1, wherein such compound is 6-fluoro-3a,11a-dihydro-8-oxo-5-(4-methyl-1-piperazinyl)-[H-cyclopenta[1,2-b]-pyrido[1,2,3-d,e]-[1,4]-benzoxazine-9-carboxylic acid of the formula

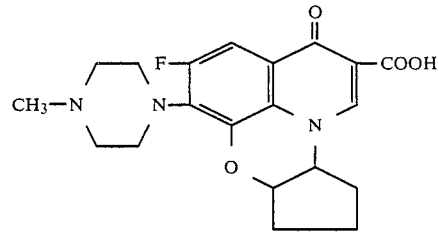

or a pharmaceutically acceptable hydrate, alkali metal, alkaline earth metal, silver or guanidinium salt or ester thereof.

4. A compound according to claim 1, wherein such compound is 6-fluoro-3a,11a-dihydro-8-oxo-5-(1-piperazinyl)-8H-cyclohepta [1,2-b]-pyrido[1,2,3-d,e]-[1,4]-benzoxazine-9carboxylic acid of the formula

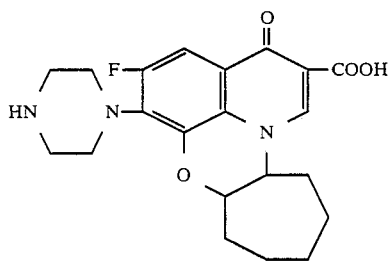

or a pharmaceutically acceptable hydrate, alkali metal, alkaline earth metal, silver or guanidinium salt or ester thereof.

5. A compound according to claim 1, wherein such compound 9-fluoro-2-fluoromethyl-2,3-dihydro-10-(1-piperazinyl)-7-oxo-7H-pyrido[1,2,3-d,e]-[1,4]-benzoxazine-6-carboxylic acid of the formula

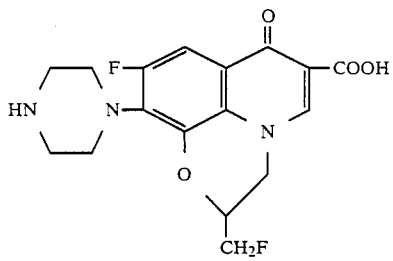

or a pharmaceutically acceptable hydrate, alkali metal, alkaline earth metal, silver or guanidinium salt or ester thereof.

* * * * *

UNITED STATES PATENT AND TRADEMARK OFFICE
CERTIFICATE OF CORRECTION

PATENT NO. : 4,847,375

DATED : July 11, 1989

INVENTOR(S) : Grohe et al.

It is certified that error appears in the above-identified patent and that said Letters Patent is hereby corrected as shown below:

| | |
|---|---|
| Title Page | INVENTION: Delete " QUINOLINE " and substitute -- QUINOLONE -- |
| Col. 1 lines 1-2 | Delete " QUINOLINE " and substitute -- QUINOLONE -- |
| Col. 1, line 53 | Delete " as " and substitute -- has -- |
| Col. 5, line 68 | Delete " benzoaxazine " and substitute -- benzoxazine -- |
| Col. 6, line 1 | Delete " 6carboxylic " and substitute -- 6-carboxylic -- |
| Col. 11, line 42 | Delete " whcih " and substitute -- which -- |
| Col. 12, line 59 | Delete " 6carboxylic " and substitute -- 6-carboxylic -- |
| Col. 12, line 68 | Delete " 9carboxylic " and substitute -- 9-carboxylic -- |
| Col. 16, lines 64-65 | Delete " ehtanol " and substitute -- ethanol -- |
| Col. 17, line 19 | Delete " cyclopental " and substitute -- cyclopenta -- |
| Col. 17, line 42 | Delete " 9carboxylic " and substitute -- 9-carboxylic -- |
| Col. 17, line 43 | Delete " 252°-4°" and substitute -- 252-4° -- |

UNITED STATES PATENT AND TRADEMARK OFFICE
CERTIFICATE OF CORRECTION

PATENT NO. : 4,847,375

DATED : July 11, 1989

INVENTOR(S) : Grohe et al.

It is certified that error appears in the above-identified patent and that said Letters Patent is hereby corrected as shown below:

Col. 19, line 41  Delete " vinyl " and substitute — phenyl —
Col. 20, line 47  Delete " H-cyclopenta " and substitute — 8H-cyclopenta —

Signed and Sealed this

Eleventh Day of June, 1991

Attest:

HARRY F. MANBECK, JR.

*Attesting Officer*   *Commissioner of Patents and Trademarks*